US011524056B2

(12) United States Patent
Romani et al.

(10) Patent No.: US 11,524,056 B2
(45) Date of Patent: *Dec. 13, 2022

(54) THYMOSIN ALPHA 1 FOR USE IN TREATMENT OF CYSTIC FIBROSIS

(71) Applicant: SciClone Pharmaceuticals International Ltd., Grand Cayman (KY)

(72) Inventors: Luigina Romani, Perugia (IT); Enrico Garaci, Rome (IT)

(73) Assignee: SciClone Pharmaceuticals International Ltd., Grand Cayman (KY)

(*) Notice: Subject to any disclaimer, the term of this patent is extended or adjusted under 35 U.S.C. 154(b) by 0 days.

This patent is subject to a terminal disclaimer.

(21) Appl. No.: 16/593,226

(22) Filed: Oct. 4, 2019

(65) Prior Publication Data

US 2020/0023039 A1 Jan. 23, 2020

Related U.S. Application Data

(63) Continuation of application No. 15/549,073, filed as application No. PCT/IT2016/000027 on Feb. 4, 2016, now Pat. No. 10,478,474.

(30) Foreign Application Priority Data

Feb. 9, 2015 (IT) .......................... RM2015A00056
Sep. 18, 2015 (IT) ........................ 102015000053089

(51) Int. Cl.
A61K 38/22 (2006.01)
A61P 11/00 (2006.01)
A61P 29/00 (2006.01)

(52) U.S. Cl.
CPC .............................. A61K 38/2292 (2013.01)

(58) Field of Classification Search
CPC combination set(s) only.
See application file for complete search history.

(56) References Cited

U.S. PATENT DOCUMENTS

| 10,478,474 | B2 | 11/2019 | Romani et al. | |
|---|---|---|---|---|
| 2007/0129292 | A1 | 6/2007 | Rasi et al. | |
| 2013/0143919 | A1* | 6/2013 | Van Goor | A61P 25/16 514/312 |

FOREIGN PATENT DOCUMENTS

| CN | 102973926 A | 3/2013 |
|---|---|---|
| JP | 2005-511563 A | 4/2005 |
| JP | 2009539916 A | 11/2009 |
| WO | WO 2004/087067 A2 | 10/2004 |
| WO | WO 2006/101740 A2 | 9/2006 |
| WO | WO 2009/033816 A2 | 3/2009 |

OTHER PUBLICATIONS

Konstan, "Ibuprofen therapy for cystic fibrosis lung disease: revisited," Current Opinion in Pulmonary Medicine 14:567-573 (2008) (Year: 2008).*
Carvalho et al., "immunotherapy of aspergillosis," clinical microbiology and infection 18: 120-125 (2012) (Year: 2012).*
Cystic fibrosis, Rosenstein, Merck Manual, accessed Feb. 4, 22 at URL merckmanuals.com/professional/pediatrics/cystic-fibrosis-cf/cystic-fibrosis?query=cystic fibrosis#, pp. 1-16 (Aug. 2021) (Year: 2021).*
Inflammation from Merck Manual, pp. 1-3. Accessed Aug. 30, 2020 (Year: 2020).*
Abdulkhaleq et al., "the crucial role of inflammatory mediators inflammation: a review,"Veterinary world 11: 627-635 (2018) (Year: 2018).*
Cantin et al., "Inflammation in cystic fibrosis lung disease: pathogenesis and therapy," Journal of cystic fibrosis 14:419-430 (2015) (Year: 2015).*
Pierluigi et al., "Thymosin α1: the regulatorof regulators?"Ann. N.Y. Acad. Sci. 1194:1-5 (2010) (Year: 2010).*
International Search Report and Written Opinion issued by the International Searching Authority for Application No. PCT/IT2016/000027, dated Jun. 6, 2016, 11 pages.
Italian Search Report and Written Opinion issued in ITRM20150056 dated May 5, 2015.
Italian Search Report and Written Opinion issued in ITUB20153714 dated Mar. 17, 2016.
Tomati et al., Thymosin α-1 does not correct F508del-CFTR in cystic fibrosis airway epitheli, JCI Insight. 3(3):e98699 (2018), 17 pages.
Database WPI Week 201351 Thomson Scientific, London, GB; AN 2013-K29145 XP002739196, & CN 102 973 926 A (Shanghai Pulmonary Hospital) Mar. 20, 2013 (Mar. 20, 2013), 1 pages.
Goldstein et al., "From lab to bedside: emerging clinical applications of thymosin [alpha]1", Expert Opinion on Biological Therapy, Informa Healthcare, Ashley, London; GB, 9(5):593-608 (2009).
Garaci et al., "Thymosin Alpha 1: From Bench to Bedside", Annals of the New York Academy of Sciences 1112(1):225-234 (2007).
Stevens et al. "Allergic Bronchopulmonary Aspergillosis in Cystic Fibrosis-State of the Art: Cystic Fibrosis Foundation Consensus Conference", Clinical Infectious Diseases, 37(s3): S225-S264 (2003).
Aaron et al., "Treatment of Aspergillus fumigatus in Patients with Cystic Fibrosis: A Randomized, Placebo-Controlled Pilot Study", Plos One 7(4):e36077 (2012), 8 pages.
Romani et al., "Thymosin alpha 1 activates dendritic cells for antifungal Th1 resistance through Toll-like receptor signaling", BLOOD 103(11):4232-4239 (2004).
McCarty et al., "A phase I randomized, multicenter trial of CPX in adult subjects with mild cystic fibrosis", Pediatric Pulmonology 33(2):90-98 (2002).
Fan et al.,"Use of thymosin alpha-1 in preparation of medicament for e.g. treating pulmonary fibrosis, and as immune modulator to increase T-helper (Th) 1 immune reaction, and for inhibiting increase of Th2 type reaction," WPI / THOMSON 2013(51) (2013).

(Continued)

Primary Examiner — Julie Ha
Assistant Examiner — Kristina M Hellman
(74) Attorney, Agent, or Firm — Cooley LLP

(57) ABSTRACT

The present invention concerns Thymosin alpha 1 (Tα1) for use in treatment of cystic fibrosis as a CFTR corrector, CFTR potentiator and anti-inflammatory agent.

10 Claims, 9 Drawing Sheets

Specification includes a Sequence Listing.

(56) References Cited

OTHER PUBLICATIONS

Camerini et al., "Historical review of thymosin [alpha] 1 in infectious diseases," Expert Opinion on Biological Therapy15(117-127) 2015.
Segal et al., "Immunotherapy for Fungal Infections," Clinical Infectious Diseases, 42(4):507-515 (2006).
Leclair et al., "Mixed bacterial-fungal infections in the CF respiratory tract," Medical Mycology 48(Suppl. I):S125-S132 (2010).
Doring et al., "Treatment of lung infection in patients with cystic fibrosis: Current and future strategies," J. Cystic Fibrosis 11:461-479 (2012).
Boyle et al., "A new era in the treatment of cystic fibrosis: correction of the underlying CFTR defect," Lancet Resp Med 1:158-163 (2013).
Ozhegov A.M et al. "Primeneniye immunomoduliatorov u detei s mucovistsidozom", Lechashchiy vrach, Jun. 10, 2010; found Aug. 5, 2019 in the Internet at https://www.lvrach.ru/2010/06/14358701/, 12 pages.
Romani et al., "Thymosin α1 Represents a Potential Potent Single-Molecule-Based Therapy for Cystic Fibrosis," Nature Medicine 23(5), 17 pages (2017).
Mathes, et al., "F508del-CFTR is not corrected by thymosin α1," Nature Medicine 24:890-893 (2018). https://doi.org/10.1038/s41591-018-Q079-6.
Extended European Search Report issued by the European Patent Office for U.S. Appl. No. 20/212,130, dated Jul. 16, 2021, 11 pages.
Romani et al., "Reply to 'F508del-CFTR is not corrected by thymosin [alpha] I'," Nature Medicine, Nature Pub. Co, New York 24(7):891-893 (2018).

* cited by examiner

THYMOSIN ALPHA 1 FOR USE IN TREATMENT OF CYSTIC FIBROSIS

CROSS-REFERENCE TO RELATED APPLICATIONS

This application is a Continuation of U.S. patent application Ser. No. 15/549,073, filed Feb. 4, 2016, which is a National Stage entry of International Patent Application Ser. No. PCT/IT2016/000027, filed Feb. 4, 2016, which claims the priority to and benefits of Italian Patent Application Nos. RM2015A00056, filed Feb. 9, 2015, and 102015000053089, filed Sep. 18, 2015. Each of these applications is herein incorporated by reference in its entirety.

INCORPORATION BY REFERENCE OF SEQUENCE LISTING

The instant application contains a Sequence Listing which has been submitted in ASCII format via EFS-Web. The contents of the text file named "SCIC-116 Sequence Listing.txt", which was prepared by Oct. 4, 2019, is 1,024 bytes in size, and is hereby incorporated by reference in its entirety.

The present invention concerns Thymosin alpha 1 (Tα1) for use in treatment of cystic fibrosis. More in particular, the present invention concerns Thymosin alpha 1 for use in treatment of cystic fibrosis as a CFTR corrector, CFTR potentiator and anti-inflammatory agent.

Cystic fibrosis (CF, OMIM 219700) is a life-threatening genetic disorder that primarily affects the lungs and digestive system. It is a life-limiting autosomal recessive disorder that affects 70,000 individuals worldwide. The outlook for patients with the disease has improved steadily over many years, largely as a result of earlier diagnosis, more aggressive therapy, and provision of care in specialised centres (1). Researchers now have a more complete understanding of the molecular-biological defect that underlies CF, which is leading to new approaches to treatment.

CF is caused by mutations in the gene encoding the CF transmembrane conductance regulator (CFTR) that regulates epithelial surface fluid secretion in respiratory and gastrointestinal tracts. CFTR cellular processing involves translation, folding at the endoplasmic reticulum, Golgi transport, post-translational modifications, apical plasma membrane targeting, and endosomal recycling and retrieval. Plasma membrane CFTR is internalized by endocytosis and then recycled to the plasma membrane or targeted for lysosomal degradation (2, 3).

Almost 2,000 variants have been reported to the Cystic Fibrosis Mutation Database (4). These mutations have been grouped into six classes: class I mutants include deletions, frameshifts and non-sense mutations that result in prematurely truncated CFTR protein products, class II mutants are defective in intracellular trafficking, class III mutants are full-length proteins with little or no ion channel activity, class IV mutants results in CFTR with only slightly reduced channel activity, and class V mutants proteins are functional but expressed at reduced levels, while class VI mutants are expressed at wild-type levels but exhibit decreased stability at the plasma membrane (5). Despite this large number of CFTR disease alleles, the vast majority (>90%) of CF patients of Northern European origin have at least one copy of a single mutant allele, ΔF508, which encodes a CFTR molecule lacking a phenylalanine at position 508. The deletion of phenylalanine at position 508 (ΔF508) in CFTR results in a temperature sensitive folding defect, retention of the protein in the endoplasmic reticulum, and subsequently targeted to the proteasome for premature degradation (6). ΔF508-CFTR folding is inefficient, with more than 99% of ΔF508-CFTR targeted for proteasomal degradation before reaching the Golgi apparatus.

Alteration of the intracellular fate of misfolded CFTR by intervention of protein folding, processing, and proteolytic pathways has shown promise for interrupting "downstream pathology". The identification of specific targets to correct defective ΔF508-CFTR folding or cellular processing (correctors) and channel gating (potentiators) provide a strategy for therapy of CF that corrects the underlying defect. Correctors could act as "pharmacological chaperones" by interacting with F508del-CFTR itself, facilitating its folding and cellular processing, or as "proteostasis regulators" by modulating the cellular quality-control machinery to alter ΔF508-CFTR recognition and processing (7). In contrast to current therapies, such as antibiotics, anti-inflammatory agents, mucolytics, nebulized hypertonic saline, and pancreatic enzyme replacement, which treat CF disease manifestations, correctors and potentiators correct the underlying CFTR anion channel defect.

So far, numerous CFTR potentiators have been identified and verified to be effective in both in vitro and in vivo studies (8, 9), although efficacies of most correctors have been somewhat disappointing. In 2012, the US FDA approved Ivacaftor (VX-770, Kalydeco, Vertex Pharmaceuticals), a potentiator that can increase CFTR-mediated chloride transport, for the treatment of CF patients with G551 D-CFTR mutation that causes only gating defect (10). Kalydeco has also been tested in patients who are homozygous for F508del-CFTR with little clinical benefit because only small amount of F508del-CFTR is targeted to the cell plasma membrane. Thereafter, a potentiator (the cyclopropane carboxamide VX-809 (Lumacaftor, by Vertex Pharmaceuticals)/Ivacaftor combination therapy (ORKAMBI) was tested in homozygous F508del-CFTR CF patients. The drug combination improved lung function 3 to 4 percent and reduced exacerbations by 35%(11). Although the study confirmed that acute Ivacaftor/Lumacaftor combination therapy could enhance Lumacaftor rescued ΔF508-CFTR activity, discouraging results have also been reported. In particular, some gating potentiators (including Ivacaftor) could reduce the correction efficacy of Lumacaftor, likely due to the destabilization of corrected ΔF508-CFTR by Ivacaftor (12).

The abrogation effect of Ivacaftor on correction efficacy of lumacaftor suggests the need for further optimization of potentiators to maximize the clinical benefit of corrector-potentiator combination therapy in CF.

In addition, given that ΔF508 should be regarded not as a simple class II mutant, but as a mixed mutant with the properties of classes II, III, and V, this suggests that a more complex therapeutic strategy must be considered or designed to correct multiple protein processing defects caused by the single ΔF508 mutation (6).

Even more, there has been no significant progress in the identification of therapeutic strategies for reversal of the lung disease from the chronic stages. It thus remains an open question if the rescue of chloride channel function is adequate to reverse the inflammatory pathology of the chronic CF lung disease (13).

Indeed, the CF gene defect (or mutation) leading to a malfunctioning CFTR protein has consequences in both epithelial and inflammatory cells of the lung, resulting in decreased chloride efflux and increased inflammatory response (14).

With regards to the excessive inflammation in the CF airways, whether the hyperinflammatory response is a result of the chronic infection or is a primary outcome of the CFTR dysfunction is still a matter of debate (15).

The defective ion and fluid transport due to CFTR mutation results in inadequate clearance of mucus and the material it traps in CF airways. The retained material results in a cycle of airways obstruction, inflammation, and infection. Accordingly, the pulmonary immune response in CF is characterized by an early and non-resolving activation of the innate immune system, which is dysregulated at several levels (16), does not result in enhanced bacterial or fungal clearance (17) and plays a pivotal role in the pathogenesis of lung disease in CF (18). The impaired eradication of bacteria early in life induces a predominantly neutrophilic inflammatory response that injures the lung and promotes airway remodeling and airway obstruction. The remarkable persistence of chronic CF lung infections despite intensive antibiotic therapy (19) has inspired some innovative approaches within which the elucidation of the initial airway inflammatory response in CF lung disease has became a priority area of translational research (20). Evidence indicate that targeting specific inflammatory/anti-inflammatory pathways may represent a valid therapeutic strategy in experimental CF (21, 22).

Only one anti-inflammatory drug (the nonsteroidal agent ibuprofen) has thus far demonstrated efficacy with an improvement in rate of decline in FEV1 over a 2-year period and a favorable risk profile; it is, therefore, recommended as a beneficial therapy for patients 7 to 18 years of age (23).

Development of anti-inflammatory therapies in CF has been challenging because their mechanism of action may be to prevent long-term clinical decline rather than to effect acute changes in more commonly used clinical outcome measures, such as lung function or frequency of pulmonary exacerbations. Despite these challenges, several therapies have currently passed into the phase 2 stage. Three examples include N-acetylcysteine, docosahexenoic acid, and sildenafil. N-acetylcysteine is an oral antioxidant medication that has been shown in one phase 2 trial to impact inflammatory measures in patients with CF and baseline inflammation, an effect hypothesized to occur by addressing a redox imbalance in neutrophils (24). A recent phase 2b clinical trial of N-acetylcysteine did demonstrate an effect on lung function, but the effect on inflammation was not reproduced (24). Similarly, docosahexaenoic acid is an omega-3 fatty acid that demonstrated antiinflammatory activity in a short clinical trial in 2003 and has completed a phase 2 trial among infants; results are forthcoming. A phase 2 trial of sildenafil is currently evaluating the effect of this oral phosphodiesterase inhibitor on markers of airway inflammation (25).

In the light of above it is therefore apparent the need to provide for new therapies for Cystic fibrosis (CF) able to overcome the disadvantages of the known therapies, including the potent anti-inflammatory drugs, corticosteroids, that are endowed with important side effects, especially growth and adrenal suppression in children (26).

The general consensus in CF therapeutics is that future therapies will aim to prevent, rather than improve, existing organ damage, including pathogenic inflammation, before patients become symptomatic.

It is clear that an ideal CF drug treatment should be capable of not only rescuing the membrane-CFTR protein but also alleviating the hyperinflammatory response and potentially attenuating the progression of the chronic CF lung disease. The identification of single compounds with dual corrector and potentiator activities, as well as anti-inflammatory activity, would be highly desirable in the field.

Thymosin alpha 1 (Tα1) is a naturally occurring polypeptide of 28 amino acid first described and characterized by Goldstein et al. in 1972 (27). Tα1 is well known in the medical field for its immunoregulatory properties in several in vitro and in vivo assay (27).

Previous use of Tα1 are already known. The peptide has been used worldwide as an adjuvant or immunotherapeutic agent to treat disparate human diseases, including viral infections, immunodeficiencies, and malignancies (28, 29). The peptide can enhance T-cell, dendritic cell and antibody responses, modulates cytokine and chemokine production and blocks steroid-induced apoptosis of thymocytes. Its central role in modulating dendritic cell function and activating multiple signaling pathways differentially contributing to different functions may offer a plausible explanation for its pleiotropic action. Additionally, the ability to activate the indoleamine 2,3-dioxygenase enzyme—conferring immune tolerance during transplantation and restraining the vicious circle that perpetuates chronic inflammation—has been a turning point, suggesting a potential, specific function in immunity (30). Accordingly, Tα1 has recently been shown to promote immune reconstitution and improve survival of recipients of HLA-matched sibling T cell-depleted stem cell transplants in a phase I/II clinical trial (31).

According to the present invention, it has been found that Tα1 has anti-inflammatory efficacy in CF patients. In fact, Tα1 was able to rectify misprocessing of the ΔF508-CFTR mutant with trafficking/stability defects; to restore the activity of chloride channel and to readdress the inflammatory/anti-inflammatory balance in murine CF by means of inhibiting the production of inflammatory (IL1β and IL1α) cytokines, increasing the production of the inflammatory-blocking cytokine IL-1 RA, promoting the protective Th1/Treg tolerogenic axis, while restraining the inflammatory Th17/Th2 axis involved in CF lung inflammation. Together, the results suggest that Tα1 correction might reach levels that affect airway epithelial function and therefore may be clinically meaningful. This, in addition to its inherent anti-inflammatory activity, makes Tα1 the ideal candidate in CF therapy.

It is therefore specific object of the present invention thymosin alpha 1 for use in treatment of cystic fibrosis. Thymosin alpha 1, in fact, can be advantageously used as CFTR corrector, CFTR potentiator and anti-inflammatory agent in patients affected by cystic fibrosis. The present invention concerns also a combination of thymosin alpha 1 with at least one agent chosen from the group consisting of antibiotic, antifungal, CFTR corrector, CFTR potentiator agent, said CFTR corrector or potentiator being other than Thymosin alpha 1, for separate or sequential use in treatment of cystic fibrosis.

According to the combination of the present invention, the antibiotic agent can be chosen for example from the group consisting of tobramycin, ciprofloxacin, colistin; the antifungal agent can be chosen for example from the group consisting of itraconazole, amphotericin B; finally, the CFTR corrector or potentiator agent other than Thymosin alpha 1 can be chosen for example from the group consisting of Ivafactor, Lumacaftor.

It is a further object of the present invention a pharmaceutical composition comprising or consisting of Thymosin alpha 1, as active principle, together with one or more excipients and/or coadjuvants for use in treatment of cystic fibrosis.

The pharmaceutical composition according to the present invention can further comprise at least one agent chosen from the group consisting of antibiotic, antifungal, CFTR corrector, CFTR potentiator agent, said CFTR corrector or potentiator being other than Thymosin alpha 1.

As mentioned above, the antibiotic agent can be chosen for example from the group consisting of tobramycin, ciprofloxacin, colistin; the antifungal agent can be chosen for example from the group consisting of itraconazole, amphotericin B; finally, the CFTR corrector or potentiator agent other than Thymosin alpha 1 can be chosen for example from the group consisting of Ivafactor, Lumacaftor.

As described above, thymosin alpha 1 shows anti-inflammatory efficacy in patients affected by Cystic Fibrosis.

It is therefore further object of the present invention thymosin alpha 1 for use in treatment and/or in prevention of inflammation in patients affected by Cystic Fibrosis.

The present invention concerns also a combination of Thymosin alpha 1 with at least one agent chosen from the group consisting of antibiotic, antifungal, CFTR corrector, CFTR potentiator agent, said CFTR corrector or potentiator being other than Thymosin alpha 1, for separate or sequential use in treatment and/or in prevention of inflammation in patients affected by Cystic Fibrosis.

According to the combination of the present invention, the antibiotic agent can be chosen for example from the group consisting of tobramycin, ciprofloxacin, colistin; the antifungal agent can be chosen for example from the group consisting of itraconazole, amphotericin B; finally, the CFTR corrector or potentiator agent other than Thymosin alpha 1 can be chosen for example from the group consisting of Ivafactor, Lumacaftor.

It is a further object of the present invention a pharmaceutical composition comprising or consisting of Thymosin alpha 1, as active principle, together with one or more eccipients and/or coadjuvants for use in treatment and/or in prevention of inflammation in patients affected by Cystic Fibrosis.

The pharmaceutical composition according to the present invention can further comprise at least one agent chosen from the group consisting of antibiotic, antifungal, CFTR corrector, CFTR potentiator agent, said CFTR corrector or potentiator being other than Thymosin alpha 1.

As mentioned above, the antibiotic agent can be chosen for example from the group consisting of tobramycin, ciprofloxacin, colistin; the antifungal agent can be chosen for example from the group consisting of itraconazole, amphotericin B; finally, the CFTR corrector or potentiator agent other than Thymosin alpha 1 can be chosen for example from the group consisting of Ivafactor, Lumacaftor.

In the use according to the invention, the terms "treat" or "treating" bear their usual meaning which includes preventing, prohibiting, alleviating, inhibiting, ameliorating, halting, restraining, slowing or reversing the progression, activation or reduction of the severity of an inflammatory-mediated disease.

According to the present invention "Separate use" is understood as meaning the administration, at the same time, of the two or more compounds of the combination according to the invention in distinct pharmaceutical forms. "Sequential use" is understood as meaning the successive administration of the two or more compounds of the composition according to the invention, each in a distinct pharmaceutical form.

An effective amount of Tα1 that is administered in an effort to treat an inflammatory reaction is that amount which is required to prevent, prohibit, alleviate, ameliorate, halt, restrain, slow or reverse the progression, or reduce the severity of said inflammatory reaction, and the daily dose to be administered will depend, according to the judgment of the primary care physician, on the subject's weight, age and general condition of the patient.

Tα1 can be administered in the form of a pharmaceutical composition in combination with pharmaceutically acceptable carriers or excipients, the proportion and nature of which are determined by the solubility and chemical properties of the compound in the carriers and/or excipients selected, the chosen route of administration, and standard pharmaceutical practice.

The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, liposome or the like.

The present invention now will be described by an illustrative, but not limitative way, according to preferred embodiments thereof, with particular reference to enclosed drawings, wherein:

FIG. 1 shows a model for CF lung disease pathophysiology. According to this model, defective ion and fluid transport due to CFTR mutation results in inadequate clearance of mucus and the material it traps in CF airways. The retained material results in a cycle of airways obstruction, inflammation, and infection. CFTR, cystic fibrosis transmembrane conductance regulator.

FIG. 2 shows a representative immunoblot of total cellular protein from control (HBE WT) and ΔF508 (HBE ΔF508) cells treated with Tα1 (A); Tα1 increased the expression of ΔF508 CFTR at PM (B); densitometric measurement of the CFTR (C band) at the PM was expressed as CFTR PM/CFTR total ratio (C); Tα1 increased the expression of CFTR (band C) in 3 (patient n. 1, 2 and 5) out 5 patients (D).

Figure 5:
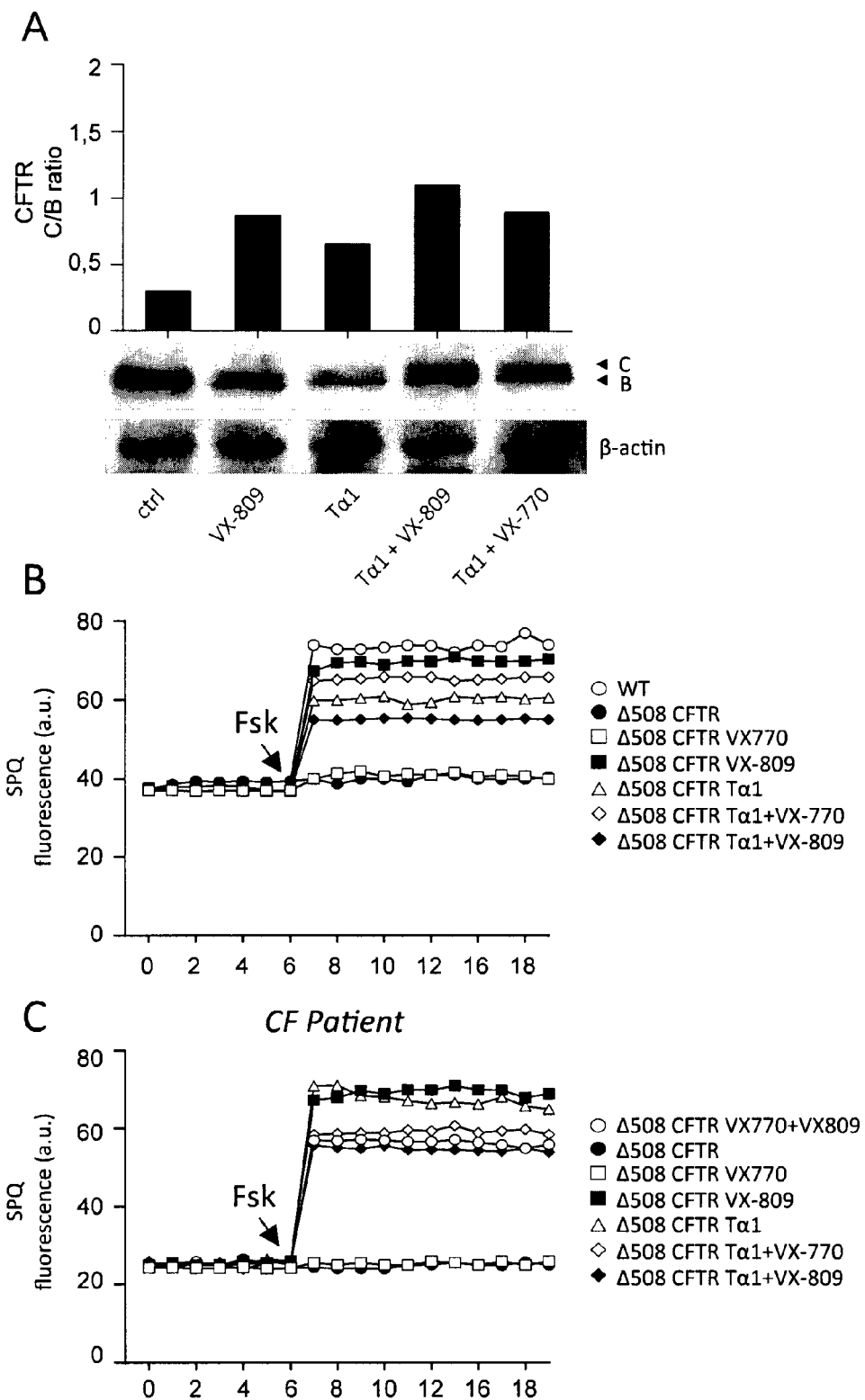

FIG. 5 shows that Tα1 increased the expression of the mature form (indicated by C) relative to the immature form (indicated by B) of CFTR in ΔF508-transfected cells (A, representative immunoblot of total cellular protein. CFTR bands were quantified by densitometry and expressed as the C/B ratio). Arrows indicate the positions of the B and C forms of CFTR based on relative mobility. TO, either alone or in combination with ivacaftor, increased the chloride permeability of ΔF508 CFTR cells between 60 to 70% relative to control (considering WT control as 100% reference value)(B, assessed by a fluorescence assay upon stimulation with fosforkolin, Fsk). Compared to lumacaftor, the activity of Tα1 was lower in CFBE41o-cells expressing ΔF508 CFTR (B) but similar in HBE cells from CF patients (C). Combined with lumacaftor, Tα1 did not increase the activity of lumacaftor (B and C).

Figure 6:
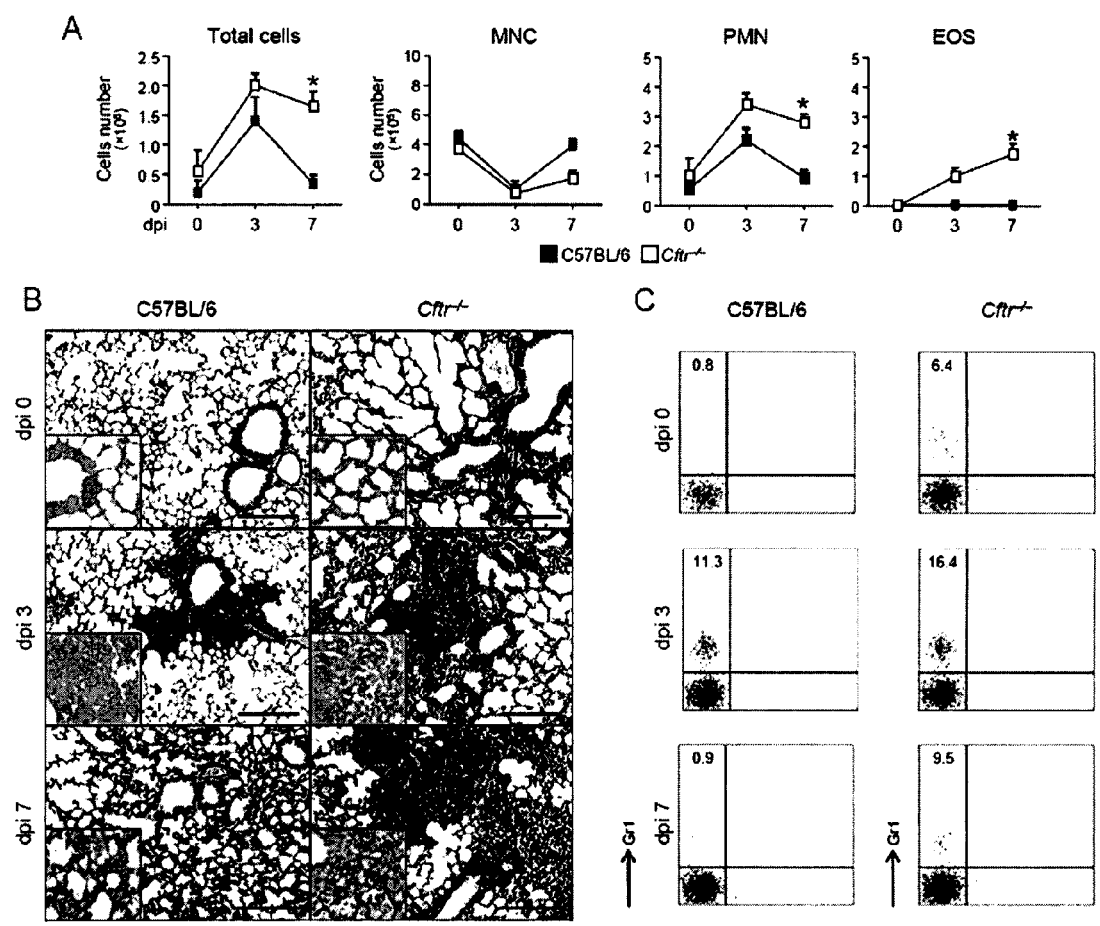

FIG. 6 shows that CF mice are susceptible to inflammatory pathology in infection. A sustained and persistent inflammatory response, characterized by neutrophil (PMN)

and eosinophils (EOS) recruitment in the BAL (A) and lung (B and C), was observed in Cftr$^{-/-}$ mice in which a degree of inflammation was already visible before the infection (C, lung histology (periodic acid-Schiff and, in the inset, Gomori staining) at different dpi). Differential cell count of mononuclear (MNC), PMN cells and EOS was determined upon May Grunwald Giemsa staining at different days post-infection (dpi). Values represent the mean+ SEM of three mice per group and are representative of 3 experiments. Photographs were taken with a high-resolution Microscopy Olympus DP71 using a ×20 objective. Scale bar 200 µm. (C) The numbers of Gr1+positive cells were assessed by flow cytometry on total lungs cells at different dpi. *P<0.05

Figure 7:
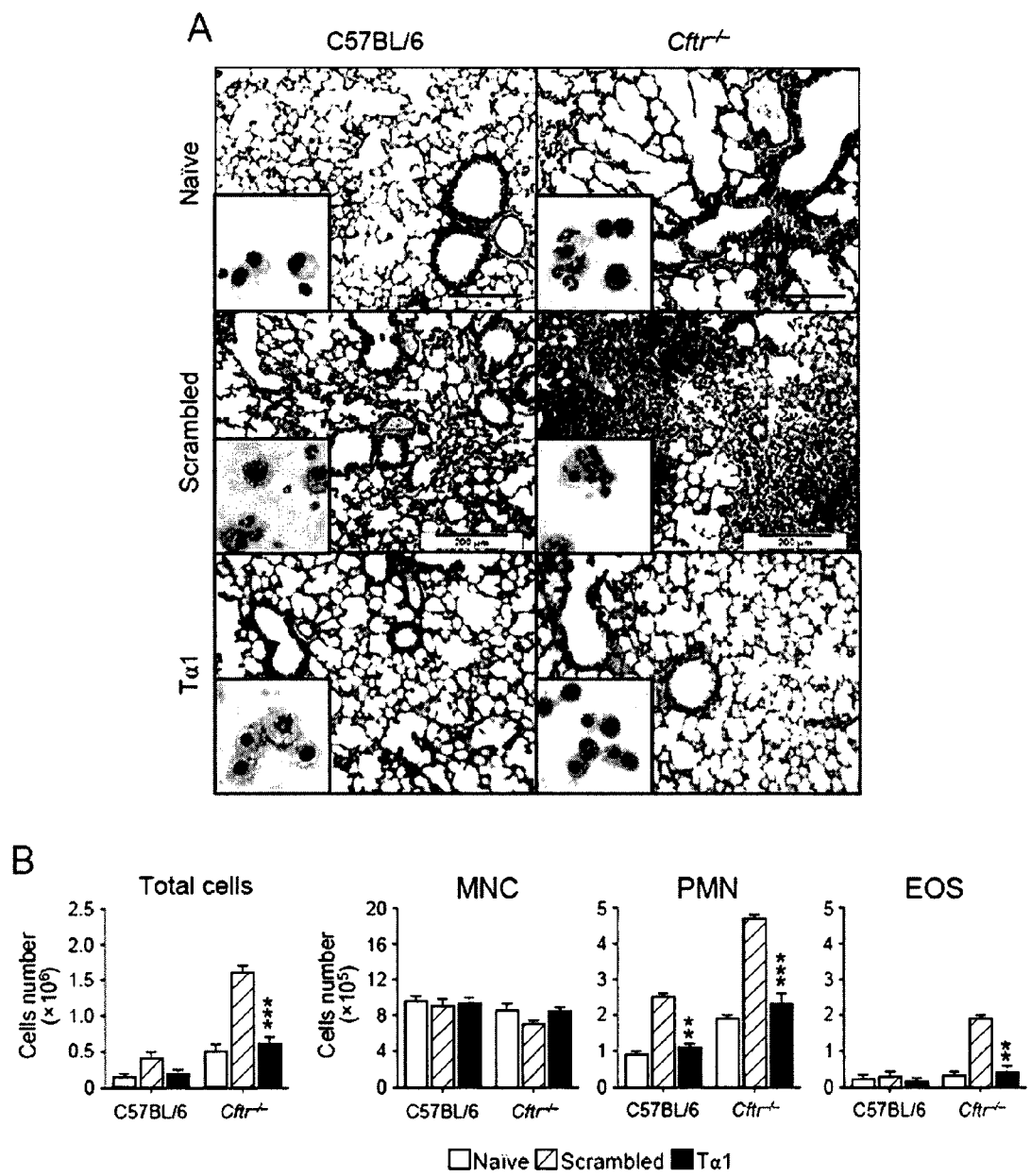

FIG. 7 shows that Tα1, protects CF mice from inflammatory pathology. Tα1, but not the scrambled peptide, significantly decreased the local inflammatory cell recruitment and lung pathology in both C57/BL6 mice and, even more, Cftr$^{-/-}$ mice, as indicated by the decreases inflammatory cell (mainly PMN, see the insets) recruitment into the lung (A) as well as in the BAL (B). (A) Lung histology (periodic acid-Schiff and, in the inset, cell recruitment). Photographs were taken with a high-resolution Microscopy Olympus DP71 using a ×20 objective. Scale bar 200 µm. (B) BAL morphometry at 7 days post-infection (dpi). Differential cell count of mononuclear (MNC), polymorphonuclear (PMN) cells and eosinophils (EOS) was determined upon May Grunwald Giemsa staining. Values represent the mean±SEM of three mice per group and are representative of 3 experiments. *P<0.05; P<0.01; *P<0.001.

Figure 8:
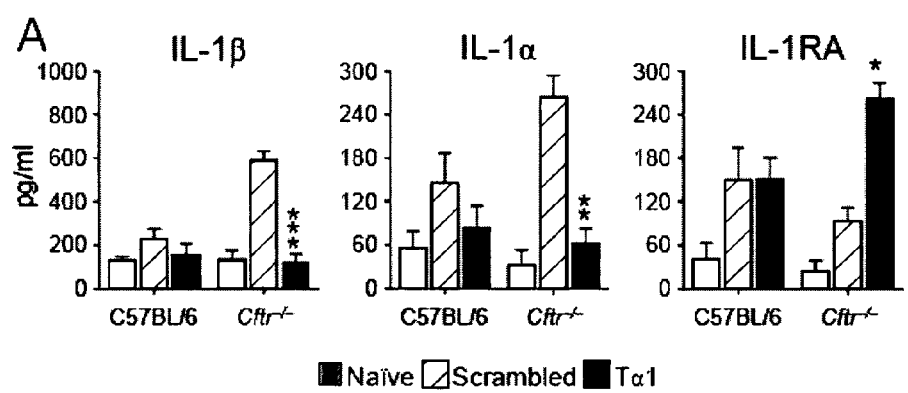

FIG. 8 shows that Tα1 down-regulates inflammatory cytokines in CF mice with aspergillosis. The levels of IL-1β, IL-1α and IL-1RA in the BAL were measured by ELISA (pg/ml) at 7 days post-infection. The results shown represent pooled data from two experiments. *P<0.05; P<0.01; *P<0.001.

Figure 9:
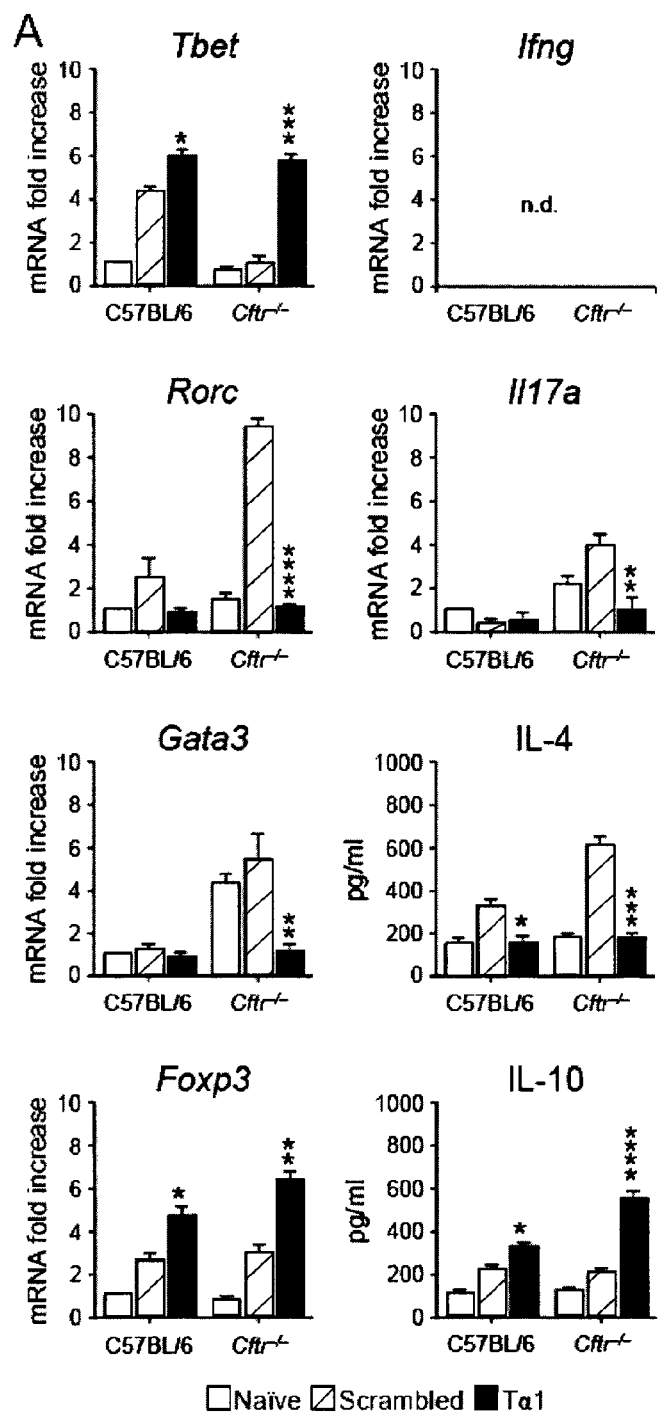

FIG. 9 shows that Tα1 regulates the Th cell balance in CF mice with aspergillosis. Tα1 decreased Th17 (decreased levels of IL-17A and of the Th17 transcription factor Rorc), Th2 (low IL-4 and Gata3) cell activation while promoting both Th1 (increased IFN-γ and Tbet) and Treg (increased IL-10 and Foxp3) cell activity. The results shown represent pooled data from two experiments. n.d. not done. *P<0.05; P<0.01; *P<0.001.

ESEMPIO 1: STUDY CONCERNING THE EFFECT OF THYMOSIN α 1 AS CFTR CORRECTOR AND PROTECTOR AND ANTI-INFLAMMATORY AGENT IN CYSTIC FIBROSIS

Materials and Methods
Cells.
Cell Lines and Cell Culture—Human bronchial epithelial (HBE) cells, homozygous for the δF508 mutation and its isogenic wild-type were obtained from lung transplants (CF patients) or lung resections (non-CF patients) (kindly provided by L J Galietta within the Italian Cystic Fibrosis Foundation). Cells were maintained at 37° C. in a humidified incubator in an atmosphere containing 5% CO2, and the experiments were done 5 days after plating(21, 22). Stable lentiviral-based transduction of the parental CFBE41o-cells (ΔF508/ΔF508), originally immortalized and characterized by Dr. D. Gruenert and co-workers(32) with either WT-CFTR or ΔF508-CFTR, was performed by Tranzyme, Inc. (Birmingham, Ala.). The transduced CFBE41o-cells were maintained in minimum Eagle's medium supplemented with 50 units/ml penicillin, 50 µg/ml streptomycin, 2 mM L-glutamine, 10% fetal bovine serum, and 1 µg/ml blasticidine (WT-CFTR) or 2 µg/ml puromycin (ΔF508-CFTR) in a 5% CO2, 95% air incubator at 37° C. The parental CFBE41o-cells were maintained under the same culture conditions but without blasticidine or puromycin. To establish polarized monolayers, CFBE41o-cells were seeded on 24-mm-diameter Transwell permeable supports (0.4 mm pore size; Corning Corp., Corning, N.Y.) at 2×10$^6$ and grown in air-liquid interface culture at 37° C. for 6-9 days and then at 27° C. for 36 hours. Cells were incubated with Tα1 100 ng/ml (CRIBI Biotechnology, Padova, see below), 3 µM VX-809 (Lumacaftor, Aurogene Rome, Italy), 1 µM VX-770 (Ivacaftor, Aurogene) alone or in combination for 24 hours before the assessment of CFTR protein expression and function. DMSO vehicle alone (0.1%, v/v) for 24 h was used as a control.

Mice.
Wild-type (WT) inbred C57BL6 mice, 8 to 12 weeks old, were purchased from Charles River Breeding Laboratories (Calco, Italy). Genetically engineered homozygote Cftr$^{-/-}$ mice (33) were bred at the Cystic Fibrosis core animal facility at San Raffaele Hospital, Milan, Italy. Experiments were performed following protocols approved by the institutional animal committee and in accordance with European Economic Community Council Directive as well as institutional animal care and use guidelines.

Infection and Treatments.
Mice were anesthetized by i.p. injection of 2.5% avertin (Sigma Chemical Co, St. Louis, Mo.) before intranasal instillation of 2×10$^7$ A. fumigatus (Af293) resting conidia/20 µl saline. For histology, paraffin-embedded tissue were stained with Periodic acid-Schiff (PAS), and BAL fluid collection was done as described (21, 22). Treatments were as follow: Tα1 and the scrambled polypeptide were supplied as purified (the endotoxin levels were <0.03 µg/ml, by a standard limulus lysate assay) sterile, lyophilized, acetylated polypeptide. The sequences were as follows: Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-O (Tα1) (SEQ ID NO:1) and Ac-Ala-Lys-Ser-Asp-Val-Lys-Ala-Glu-Thr-Ser-Ser-Glu-Ile-Asp-Thr-Thr-Glu-Leu-Asp-Glu-Lys-Val-Glu-Val-Lys-Ala-Asn-Glu-OH (scrambled peptide) (SEQ ID NO:2). The lyophilized powders were reconstituted in sterile water and 200 µg/kg/i.p. were given daily for 6 consecutive days beginning the day of the infection.

Flow Cytometry.
Staining for cell antigen expression was done as described (21, 22). Cells are analyzed with a FACScan flow cytofluorometer (Becton Dickinson, Mountain View, Calif.) equipped with CELLQuest™ software. Before labeling, FcR blocking was performed. Control staining of cells with irrelevant antibodies is used to obtain background fluorescence values. Data are expressed as a percentage of positive cells over total cells analyzed.

CFTR Immunoblot Analysis.
Immunoblot techniques using the anti-CFTR antibody (clone CF3, Abcam) were used to measure CFTR maturation in FRT, HEK-293, or HBE cells expressing CFTR or F508del-CFTR (34). After incubation, cells were harvested in ice-cold D-PBS solution (without calcium and magnesium) and pelleted at 1,000×g at 4° C. Cell pellets were lysed in 1% Nonidet P-40, 0.5% sodium deoxycholate, 200 mM NaCl, 10 mM Tris, pH 7.8, and 1 mM EDTA plus protease inhibitor mixture (1:250; Roche) for 30 min on ice. Lysates were spun for 10 min at 10,000×g at 4° C. to pellet nuclei and insoluble material. Approximately 12 µg total protein was heated in Laemmli buffer with 5% β-mercaptoethanol at 37° C. for 5 min and loaded onto a 3% to 8% Tris-acetate gel (Invitrogen). The gel was transferred to nitrocellulose and processed for Western blotting by using monoclonal CFTR antibody or polyclonal to β-actin (Santa Cruz Biotechnology). Blots were developed by enhanced chemiluminescence. LiteAblotPlus chemiluminescence substrate (Euroclone S.p.A.), using ChemiDoc™ XRS+ Imagig system (Bio-Rad Laboratories) and blot quantification was obtained by densitometry image analysis using Image Lab 3.1.1 software (Bio-Rad).

Activation of CFTR.

Because the CFTR channel is permeable to iodide, it is possible to determine the efflux of this ion from previously loaded cells by a colorimetric assay using the SPQ (6-methoxy-N-(3-sulfopropyl) quinolinium) fluorescent probe (35).

Reverse Transcriptase-Polymerase Chain Reaction (RT-PCR).

Total RNA extraction and synthesis and PCR of cDNA were done on total lung cells as described (21, 22). Amplification efficiencies were validated and normalized against Gapdh. The thermal profile for SYBR Green real-time PCR was at 95° C. for 3 min, followed by 40 cycles of denaturation for 30 s at 95° C. and an annealing/extension step of 30 s at 60° C. Each data point was examined for integrity by analysis of the amplification plot. The mRNA-normalized data were expressed as relative mRNA in treated cells compared to that of unstimulated cells.

Cytokine Determination by ELISA.

Cytokine levels in lung homogenates from treated and untreated mice were determined by cytokine-specific ELISA (R&D Systems, Inc. Space Import-Export srl, Milan, Italy) as described (21, 22)

Statistical Analyses.

Student's paired t test was used to determine the significance of values in experimental samples (significance was defined as P<0.05). Survival data were analyzed using the Mann-Whitney U test. In vivo groups consisted of 6 animals. Unless otherwise indicated, data are mean±SE. Data were analyzed by GraphPad Prism 4.03 program (GraphPad Software).

Results

Tα1 Acts as a Corrector by Increasing Cell Surface Expression of ΔF508-CFTR in CF Cells.

Figure 1:
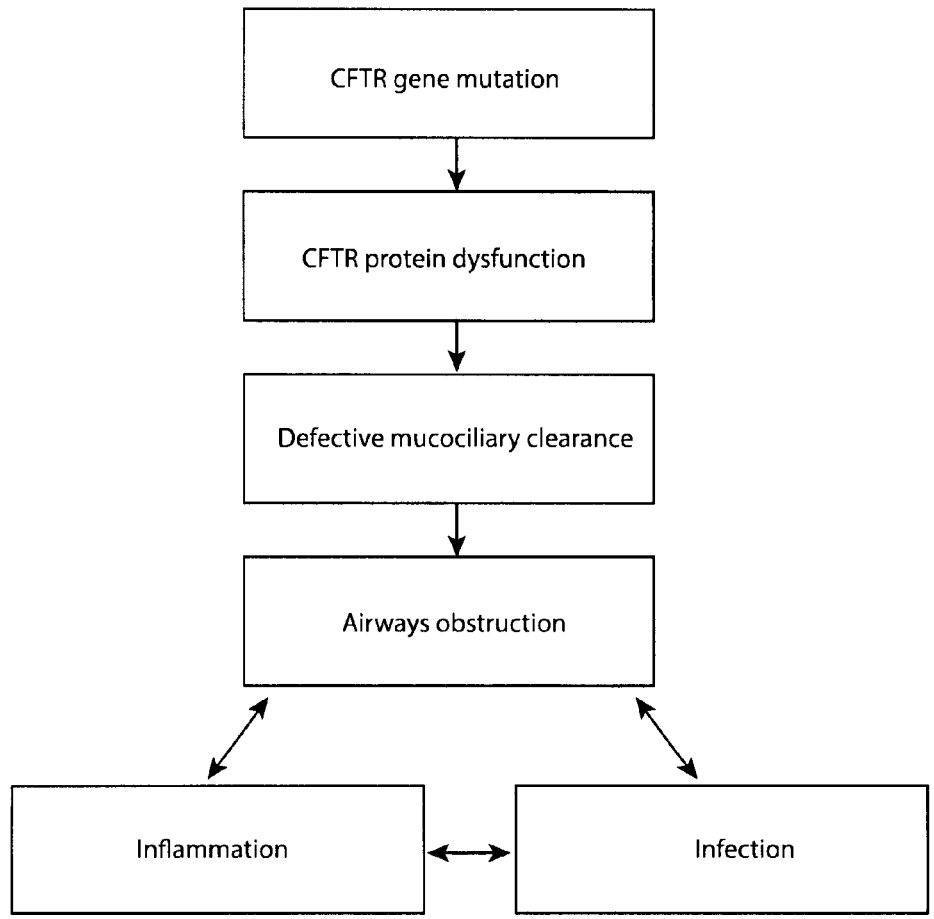
Figure 2:
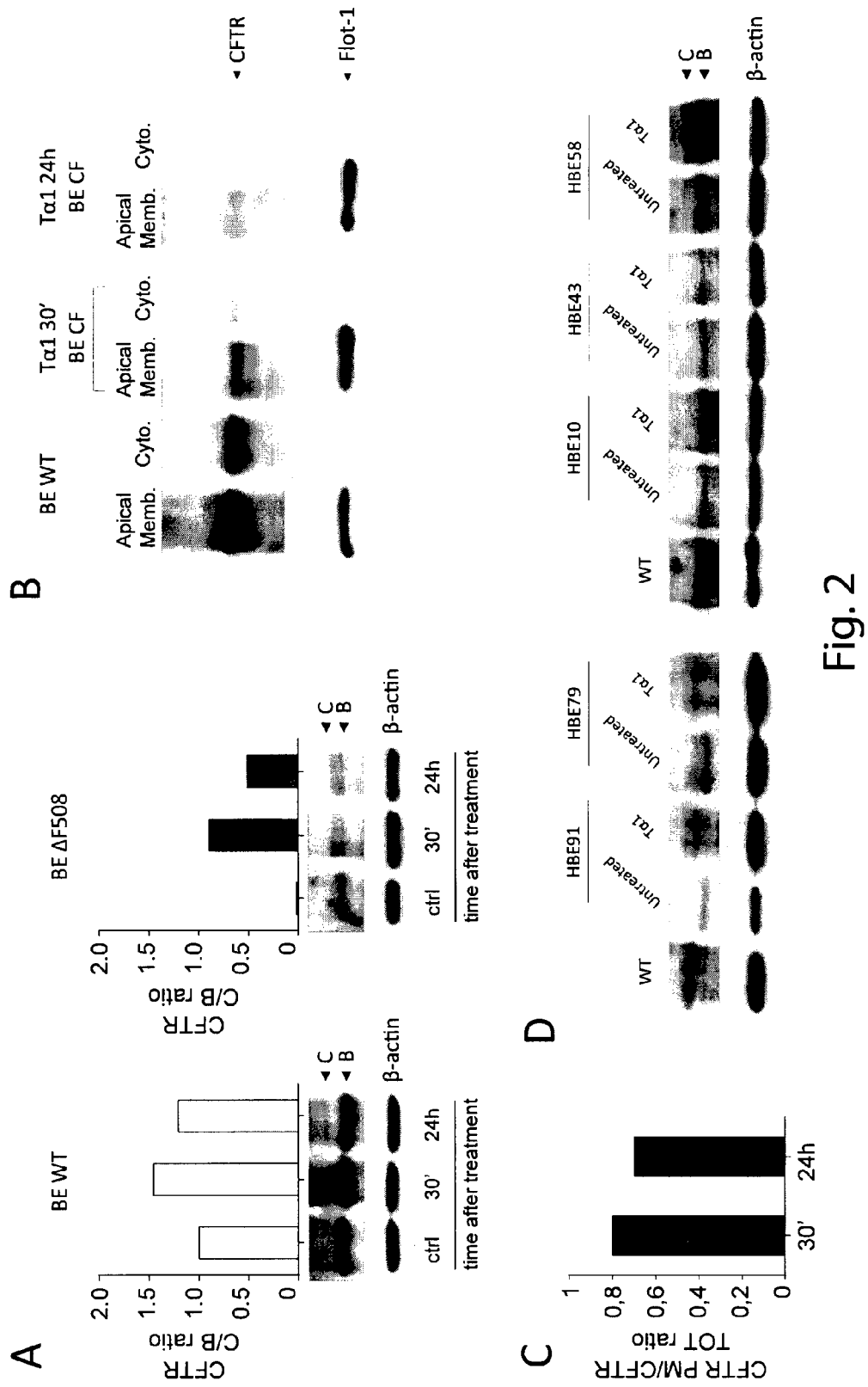

The SV40 transformed CF airway epithelial cell line (CFBE410-), homozygous for the ΔF508-CFTR mutation, was used (32). CFBE410 cells stably expressing ΔF508 CFTR or WT CFTR were treated with 100 ng/ml of Tα1 for 30 mins to 24 hours. FIG. 2 shows a representative immunoblot of total cellular protein from control (HBE WT) and ΔF508 (HBE ΔF508) cells treated with Tα1 (Panel A, FIG. 2). Immunoblot techniques were used to measure ΔF508-CFTR exit from the endoplasmic reticulum and passage through the Golgi, which is characterized by an increase in the molecular weight of CFTR (from a 135-140-kDa band to a 170-180-kDa band) as a result of glycosylation. After CFTR is processed by the Golgi, the mature, complex-glycosylated CFTR form is delivered to the cell surface. Tα1 persistently increased the cellular expression of ΔF508 mature CFTR (indicated by C), from as early as 30 mins after the exposure until 24 hours later, as opposed to WT CFTR. CFTR bands were quantified by densitometry and expressed as the C/B ratio. In FIG. 2, arrows indicate the positions of the C (mature) and B (immature) forms of CFTR based on relative mobility. To prove that the increased expression of ΔF508 CFTR correlated with its increased trafficking and stability at plasma membrane (PM), PM proteins were purified from cytosolic components from cells treated with Tα1 as above. The fractions were immunoblotted with anti-CFTR antibody and FLOT1 (clone C-2 Santa Cruz Biotechnology) was used to confirm cell surface protein-specific localization. The results show that Tα1 increased the expression of ΔF508 CFTR at PM (Panel B, FIG. 2). Densitometric measurement of the CFTR (C band) at the PM was expressed as CFTR PM/CFTR total ratio (Panel C, FIG. 2). To assess whether Tα1 also increased the expression of CFTR in CF patients, bronchoalveolar cells (HBE, human BE) from 5 CF patients were treated with 100 ng/ml of Tα1 for 24 hours and assessed for CFTR protein expression. The results show that Tα1 increased the expression of CFTR (band C) in 3 (patient n. 1, 2 and 5) out 5 patients (Panel D, FIG. 2). These results indicate that Tα1 increases ΔF508 CFTR maturation resulting in increased cell surface density and stability and qualify Tα1 as corrector.

Tα1 Acts as Potentiator by Increasing the Functional Activity of ΔF508-CFTR in CF Cells.

Figure 3:
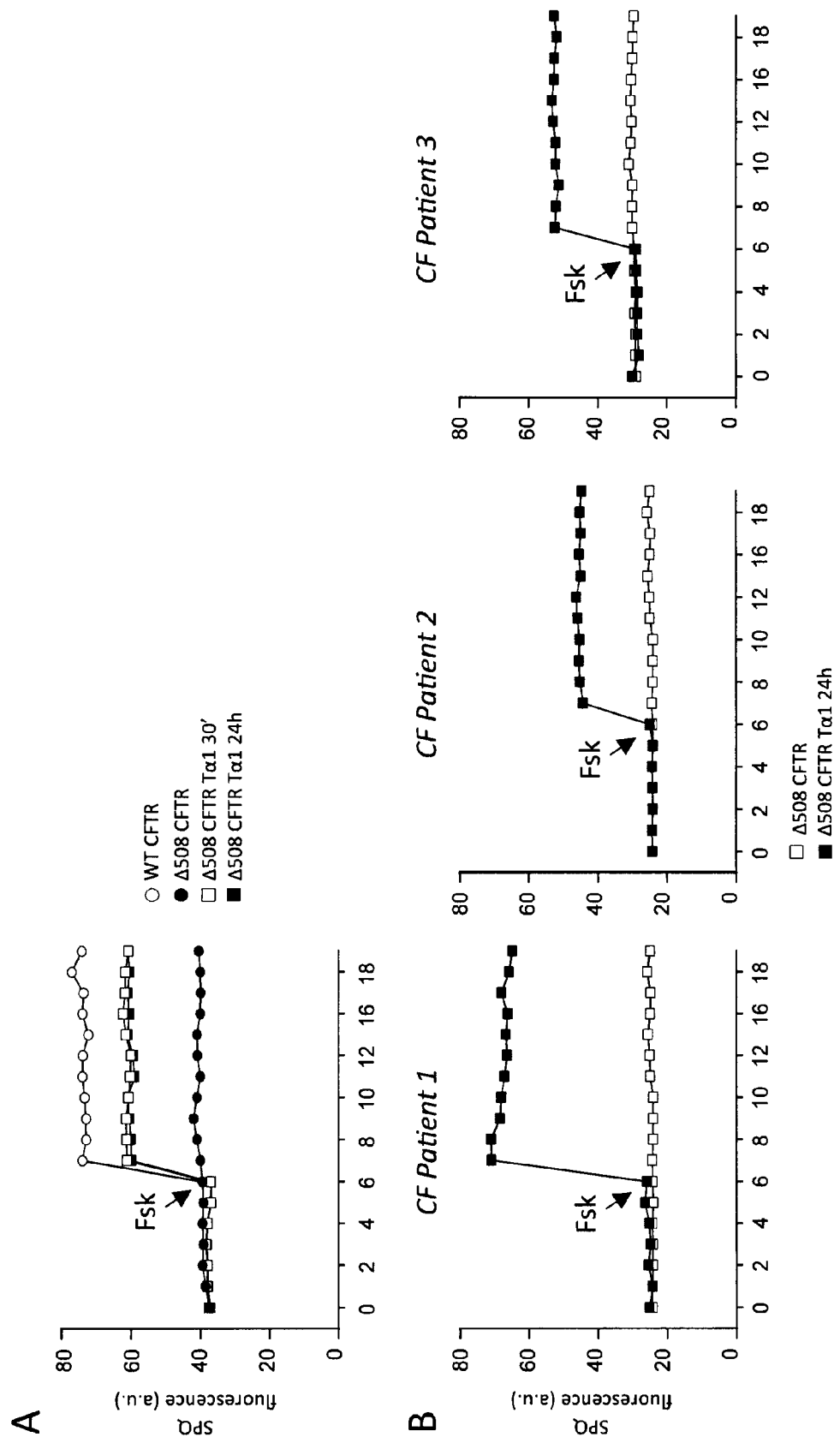
FIG. 3 shows that Tα1 increased chloride permeability of ΔF508 CFTR cells to approximately 70% relative to control (considering WT control as 100% reference value) in CFBE 41o-cells(A) and HBE cells from CF patients(B).

Potentiators are intended to restore cAMP-dependent chloride channel activity of mutant CFTR at the cell surface. Restoring even less than 30% of CFTR function in vivo (between 5 to 30%) is believed to confer an at least partial clinical benefit to CF patients by improving lung function (36). To assess the Cl⁻ channel activity of Tα1, CFBE41o-cells and HBE cells from CF patients were treated with 100 ng/ml of Tα1 for 24 hours and assessed for chloride transport by the use of the halide-sensitive fluorescent probes (6-methoxy-N-(-sulphopropyl)quinolinium (SPQ) upon stimulation with forskolin to activate CFTR through the cAMP/PKA pathway (35). The results show that Tα1 increased chloride permeability of ΔF508 CFTR cells to approximately 70% relative to control (considering WT control as 100% reference value) in CFBE 41o-cells (Panel A, FIG. 3) and HBE cells from CF patients (Panel B, FIG. 3). Thus, Tα1 significantly increased CFTR-mediated chloride permeability in association with increased levels of membrane-associated CFTR.

Tα1 Induces the Expression of the Alternative Ion Channel TMEM16A.

Figure 4:
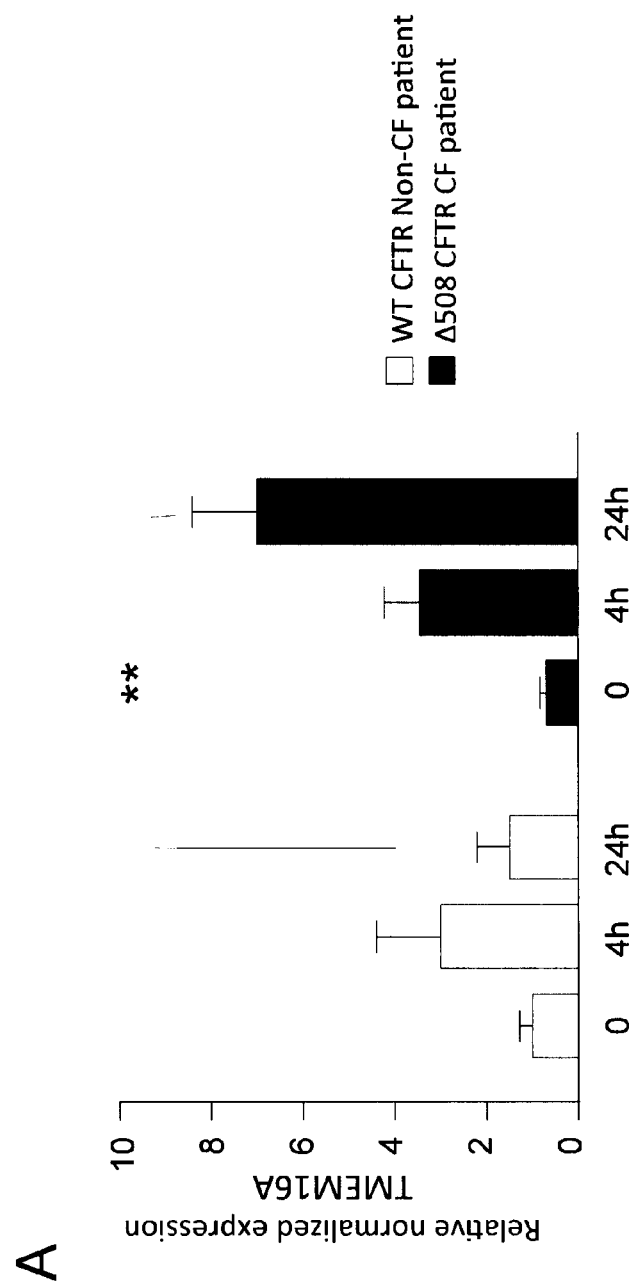
FIG. 4 shows that Tα1 markedly increased TMEM16A expression in control and CF cells after 4 hours of exposure. However, while the TMEM16A expression returned to baseline levels in control cells at 24 hours, it remains elevated in CF cells (A).

Pharmacological correction of the ion transport defect by targeting of mutant CFTR, or alternative ion channels that may compensate for CFTR dysfunction, has long been considered as an attractive approach to a causal therapy of CF(37). TMEM16A, a $Ca^{2+}$-activated Cl⁻channel, is associated with calcium-dependent chloride current(38) and, although distinct from CFTR, shows functional and molecular interaction with CFTR(39). Activation of TMEM16A with pharmacological agents could circumvent the primary defect in CF, irrespective of CFTR genotype(40). DNA microarray analysis has indicated that the expression of TMEM16A was greatly increased in mice with pulmonary aspergilosis upon treatment with Tα1 (unpublished results). Based upon these findings, whether TMEM16A expression was induced by Tα1 on HBE cells from control or CF patients has been evaluated. To this purpose cells have been exposed to 100 ng/ml of Tα1 up to 24 hours and assessed TMEM16A mRNA expression by RT-PCR on total RNA from cells. The results show that Tα1 markedly increased TMEM16A expression in control and CF cells after 4 hours of exposure. However, while the TMEM16A expression returned to baseline levels in control cells at 24 hours, it remains elevated in CF cells (FIG. 4A). These results suggest that Tα1, by inducing the expression of the alternative Cl⁻ channel TMEM 16A, could further ameliorate ion channel activity in CF.

Tα1, Either Alone or in Combination with the Potentiator Ivacaftor, Rescues ΔF508 CFTR Activity to an Extent Similar to the Corrector Lumacaftor.

The activity of Tα1, either alone or in combination with ivacaftor, has been comparatively assessed with that of lumacaftor on CFBE410-cells expressing ΔF508 CFTR and on HBE cells from CF patients. To this purpose, cells were treated with Tα1 (100 ng/ml), VX-770 (1 μM) or VX-809 (3 μM) alone or in combination for 24 hours and assessed for CFTR protein expression and function. The results show that, similar to lumacaftor, Tα1 increased the expression of the mature form (indicated by C) relative to the immature form (indicated by B) of CFTR in ΔF508-transfected cells (A, representative immunoblot of total cellular protein (FIG. 5). CFTR bands were quantified by densitometry and expressed as the C/B ratio). Arrows in FIG. 5 indicate the positions of the B and C forms of CFTR based on relative mobility). Ivacaftor did not increased CFTR expression, but the combination of Tα1/ivacaftor did so. In terms of ion channel activity, Tα1, either alone or in combination with ivacaftor, increased the chloride permeability of ΔF508 CFTR cells between 60 to 70% relative to control (considering WT control as 100% reference value)(B, assessed by a fluorescence assay upon stimulation with fosforkolin, Fsk). Compared to lumacaftor, the activity of Tα1 was lower in CFBE41o-cells expressing ΔF508 CFTR (B) but similar in HBE cells from CF patients (C). Combined with lumacaftor, Tα1 did not increase the activity of lumacaftor (B and C). These results indicate the ability of Tα1 to increase CFTR expression was comparable to that of lumacaftor and could be exploited for combination therapy with ivacaftor.

CF Mice are Susceptible to Inflammatory Pathology in Infection.

To assess the therapeutic activity of Tα1 in CF, the susceptibility of C57BL/6 and Cftr$^{-/-}$ mice to the inflammatory pathology associated with the infection with *Aspergillus fumigatus*, a known microbial colonizer of the airways of CF patients(41), has been evaluated. C57BL/6 and Cftr$^{-/-}$ mice were infected intranasally with live *A. fumigatus* conidia and assessed for parameters of inflammation. A sustained and persistent inflammatory response, characterized by neutrophil (PMN) and eosinophils (EOS) recruitment in the BAL (Panel A, FIG. 6) and lung (Panels B and C, FIG. 6), was observed in Cftr$^{-/-}$ mice in which a degree of inflammation was already visible before the infection (C, lung histology (periodic acid-Schiff and, in the inset, Gomori staining) at different dpi). Differential cell count of mononuclear (MNC), PMN cells and EOS was determined upon May Grunwald Giemsa staining at different days post-infection (dpi). Values represent the mean+ SEM of three mice per group and are representative of 3 experiments. Photographs were taken with a high-resolution Microscopy Olympus DP71 using a ×20 objective. Scale bar 200 μm. (C) The numbers of Gr1+positive cells were assessed by flow cytometry on total lungs cells at different dpi. *P<0.05

Tα1 Protects CF Mice from Inflammatory Pathology.

CF mice are susceptible to the inflammatory response associated with *Aspergillus* infection and allergy and thus represent a suitable model to evaluate the effects of Tα1.

*Aspergillus*-infected mice were treated with 200 μg/kg/i.p. daily of Tα1 for 6 consecutive days beginning the day of the infection. Mice were monitored for lung inflammatory pathology and cell recruitment at 7 days post-infection. Tα1, but not the scrambled peptide, significantly decreased the local inflammatory cell recruitment and lung pathology in both C57/BL6 mice and, even more, Cftr$^{-/-}$ mice, as indicated by the decreases inflammatory cell (mainly PMN, see the insets) recruitment into the lung (Panel A, FIG. 7) as well as in the BAL (Panel B, FIG. 7). These data indicate that Tα1 is effective in limiting inflammatory cell recruitment in the lung of CF mice during infection. (A) Lung histology (periodic acid-Schiff and, in the inset, cell recruitment). Photographs were taken with a high-resolution Microscopy Olympus DP71 using a ×20 objective. Scale bar 200 μm. (B) BAL morphometry at 7 days post-infection (dpi). Differential cell count of mononuclear (MNC), polymorphonuclear (PMN) cells and eosinophils (EOS) was determined upon May Grunwald Giemsa staining. Values represent the mean±SEM of three mice per group and are representative of 3 experiments. *P<0.05; P<0.01; *P<0.001.

Tα1 Down-Regulates Inflammatory Cytokines in CF Mice with Aspergillosis.

C57BL/6 and Cftr$^{-/-}$ mice were infected intranasally with live *A. fumigatus* conidia and treated with 200 μg/kg/i.p. Tα1 daily for 6 consecutive days beginning the day of the infection. The results are showed in FIG. 8. They show that the heightened and unresolved inflammatory response in Cftr$^{-/-}$ mice was associated with higher levels, as compared to C57/BL6 of IL-1β and IL-1α in the BAL during infection. Upon Tα1 treatment, the levels of both IL-1β and IL-1α sharply decreased in either type of mice and, of great interest, the levels of the inflammatory-blocking cytokine (IL-1RA) increased. Given that high levels of IL-1β and IL-1α are observed in patients with CF(42), these data indicate that Tα1 may contribute to the local inflammatory/anti-inflammatory cytokine balance in patients with CF. The levels of IL-1β, IL-1α and IL-1RA in the BAL were measured by ELISA (μg/ml) at 7 days post-infection. The results shown represent pooled data from two experiments. *P<0.05; P<0.01; *P<0.001.

Tα1 Regulates the Th Cell Balance in CF Mice with Aspergillosis.

The inflammatory Th17 pathway is involved in CF lung inflammation (21, 22, 43) while the Th2 pathway is associated with CF fungal allergy(44). For the assessment of the effects of Tα1 on Th cell activation, levels of Th cytokines in the lungs and of the corresponding transcription factors in the draining thoracic lymph nodes have been measured in C57BL/6 and Cftr$^{-/-}$ mice infected and treated with Tα1 as above. Tα1 decreased Th17 (decreased levels of IL-17A and of the Th17 transcription factor Rorc), Th2 (low IL-4 and Gata3) cell activation while promoting both Th1 (increased IFN-γ and Tbet) and Treg (increased IL-10 and Foxp3) cell activity. These results indicate that Tα1 is a potent activator of the anti-inflammatory Th1/Treg axis in CF while restraining the activation of inflammatory Th17/Th2 cells (FIG. 9). The cytokine levels were assessed in lung homogenates (by ELISA or RT-PCR) and the expression of the corresponding Th transcription factors (by RT-PCR) in the draining thoracic lymph nodes. The results shown represent pooled data from two experiments. n.d. not done. *P<0.05; P<0.01; *P<0.001.

REFERENCES

1. O'Sullivan B P, Freedman S D. Cystic fibrosis. Lancet 2009; 373: 1891-1904.
2. Welsh M J, Smith A E. Molecular mechanisms of CFTR chloride channel dysfunction in cystic fibrosis. Cell. 1993; 73:1251-1254.
3. Guggino W B, Stanton B A. New insights into cystic fibrosis: molecular switches that regulate CFTR. Nature Rev. Mol. Cell. Biol. 2006; 7:426-436.
4. Cystic Fibrosis Foundation. Cystic Fibrosis Foundation Patient Registry Annual Data Report 2011. Cystic Fibrosis Foundation; 2012.
5. The Cystic Fibrosis Genotype-Phenotype Consortium Correlation between genotype and phenotype in patients with cystic fibrosis. N. Engl. J. Med. 1993; 329:1308-1313.
6. Cutting G R. Cystic fibrosis genetics: from molecular understanding to clinical application Nat Rev Genet. 2015; 16: 45-56.
7. Mall M A, Galietta L J. Targeting ion channels in cystic fibrosis. J Cyst Fibros. 2015. pii: S1569-1993 (15)00150-2.
8. Pettit R S, Fellner C. CFTR modultators for the treatment of Cystic fibrosis. P&T 2014; 39:500-511.

9. Yang H, Ma T. F508del-cystic fibrosis transmembrane regulator correctors for treatment of cystic fibrosis: a patent review. Expert Opin. Ther. Patents 2015;
10. Ramsey B W, Davies J, McElvaney N G, Tullis E, Bell S C, Dřevínek P, Griese M, McKone E F, Wainwright C E, Konstan M W, Moss R, Ratjen F, Sermet-Gaudelus I, Rowe S M, Dong Q, Rodriguez S, Yen K, Ordoñez C, Elborn J S.
11. Wainwright C E, Elborn J S, Ramsey B W, Marigowda G, Huang X, Cipolli M, Colombo C, Davies J C, De Boeck K, Flume P A, Konstan M W, McColley S A, McCoy K, McKone E F, Munck A, Ratjen F, Rowe S M, Waltz D, Boyle M P; TRAFFIC Study Group; TRANSPORT Study Group. Lumacaftor-Ivacaftor in Patients with Cystic Fibrosis Homozygous for Phe508del CFTR. N Engl J Med. 2015; 373:220-31.
12. Cholon D M, Quinney N L, Fulcher M L, Esther C R Jr, Das J, Dokholyan N V, Randell S H, Boucher R C, Gentzsch M. Potentiator ivacaftor abrogates pharmacological correction of ΔF508 CFTR in cystic fibrosis. Sci Transl Med. 2014; 6:246ra96.
13. Corvol H, Thompson K E, Tabary O, le Rouzic P, Guillot L. Translating the genetics of cystic fibrosis to personalized medicine. Transl Res. 2015 Apr. 15. pii: S1931-5244 (15)00131-0.
14. Belcher C N, Vij N. Protein processing and inflammatory signaling in Cystic Fibrosis: challenges and therapeutic strategies. Curr Mol Med. 2010; 10:82-94.
15. Cantin A M, Hartl D, Konstan M W, Chmiel J F. Inflammation in cystic fibrosis lung disease: Pathogenesis and therapy. J Cyst Fibros. 2015 July; 14:419-30).
16. Hartl D, Gaggar A, Bruscia E, et al. Innate immunity in cystic fibrosis lung disease. J Cyst Fibros 2012; 11: 363-382.
17. Mizgerd J P, Lupa M M, Kogan M S, et al. Nuclear factor-kappaB p50 limits inflammation and prevents lung injury during *Escherichia coli* pneumonia. Am J Respir Crit Care Med 2003; 168: 810-817.
18. Cohen T S, Prince A. Cystic fibrosis: a mucosal immunodeficiency syndrome. Nat Med 2012; 18: 509-519.
19. Hoffman L R, Ramsey B W. Cystic fibrosis therapeutics: the road ahead. Chest 2013; 143: 207-213.
20. Ramsey B, Banks-Schlegel S, Accurso F, et al. Future Directions in Early Cystic Fibrosis Lung Disease Research. Am J Respir Crit Care Med 2012; 185: 887-892.
21. Iannitti R G, Carvalho A, Cunha C, et al. Th17/Treg imbalance in murine cystic fibrosis is linked to indoleamine 2,3-dioxygenase deficiency but corrected by kynurenines. Am J Respir Crit Care Med 2013; 187: 609-620.
22. Iannitti R G, Casagrande A, De Luca A, et al. Hypoxia promotes danger-mediated inflammation via receptor for advanced glycation end products in cystic fibrosis. Am J Respir Crit Care Med 2013; 188: 1338-1350.
23. Lands L C, Stanojevic S. Oral non-steroidal anti-inflammatory drug therapy for lung disease in cystic fibrosis. Cochrane Database Syst Rev. 2013 Jun. 13; 6:CD001505.
24. Conrad C, Lymp J, Thompson V, Dunn C, Davies Z, Chatfield B, Nichols D, Clancy J, Vender R, Egan M E, Quittell L, Michelson P, Antony V, Spahr J, Rubenstein R C, Moss R B, Herzenberg L A, Goss C H, Tirouvanziam R. Long-term treatment with oral N-acetylcysteine: affects lung function but not sputum inflammation in cystic fibrosis subjects. A phase II randomized placebo-controlled trial. J Cyst Fibros. 2015; 14:219-27.
25. P. J. Mogayzel Jr., E. T. Naureckas, K. A. Robinson, G. Mueller, D. Hadjiliadis, J. B. Hoag, et al. Cystic fibrosis pulmonary guidelines. Chronic medications for maintenance of lung health Am J Respir Crit Care Med. 2013 187. 680-689.
26. De Benedictis F M, Bush A. Corticosteroids in respiratory diseases in children. Am J Respir Crit Care Med. 2012; 185:12-23.
27. Goldstein A L, Guha A, Zatz M M, et al. Purification and biological activity of thymosin, a hormone of the thymus gland. Proc Natl Acad Sci USA 1972; 69: 1800-1803.
28. Garaci E., Pica F., Rasi G., et al Combination therapy with BRM in cancer and infections disease. Mech. Ageing Dev, 1997, 96, 103-116.
29. Tuthill C, Rios I, McBeath R. Thymosin alpha 1: past clinical experience and future promise. Ann N Y Acad Sci 2010; 1194: 130-135.
30. Romani L, Bistoni F, Perruccio K, et al. Thymosin alpha1 activates dendritic cell tryptophan catabolism and establishes a regulatory environment for balance of inflammation and tolerance. Blood 2006; 108: 2265-2274.
31. Perruccio K, Bonifazi P, Topini F, et al. Thymosin alpha1 to harness immunity to pathogens after haploidentical hematopoietic transplantation. Ann N Y Acad Sci 2010; 1194: 153-161.
32. Bruscia E, Sangiuolo F, Sinibaldi P, Goncz K K, Novelli G, Gruenert D C. Isolation of C F cell lines corrected at DeltaF508-CFTR locus by SFHR-mediated targeting. Gene Ther. 2002; 9:683-5.
33. Zhou L, Dey C R, Wert S E, et al. Correction of lethal intestinal defect in a mouse model of cystic fibrosis by human CFTR. Science 1994; 266: 1705-1708.
34. Van Goor F, Hadida S, Grootenhuis P D, Burton B, Stack J H, Straley K S, Decker C J, Miller M, McCartney J, Olson E R, Wine J J, Frizzell R A, Ashlock M, Negulescu P A. Correction of the F508del-CFTR protein processing defect in vitro by the investigational drug VX-809. Proc Natl Acad Sci USA. 2011; 108:18843-8.
35. Munkonge F1, Alton E W, Andersson C, Davidson H, Dragomir A, Edelman A, Farley R, Hjelte L, McLachlan G, Stern M, Roomans G M.
   Measurement of halide efflux from cultured and primary airway epithe lial cells using fluorescence indicators. J Cyst Fibros. 2004; 3 Suppl 2:171-6.
36. Ramalho AS1, Beck S, Meyer M, Penque D, Cutting G R, Amaral M D. Five percent of normal cystic fibrosis transmembrane conductance regulator mRNA ameliorates the severity of pulmonary disease in cystic fibrosis. Am J Respir Cell Mol Biol. 2002; 27:619-27).
37. Mall M A, Galietta L J. Targeting ion channels in cystic fibrosis. J Cyst Fibros. 2015 23. pii: S1569-1993 (15) 00150-2.
38. Caputo A1, Caci E, Ferrera L, Pedemonte N, Barsanti C, Sondo E, Pfeffer U, Ravazzolo R, Zegarra-Moran O, Galietta L J. TMEM16A, a membrane protein associated with calcium-dependent chloride channel activity. Science. 2008; 322:590-4.
39. Ousingsawat J, Kongsuphol P, Schreiber R, Kunzelmann K. CFTR and TMEM16A are separate but functionally related Cl-channels. Cell Physiol Biochem. 2011; 28(4): 715-24).
40. Sondo E, Caci E, Galietta L J. The TMEM16A chloride channel as an alternative therapeutic target in cystic fibrosis. Int J Biochem Cell Biol. 2014; 52:73-6.
41. Felton I C, Simmonds N J. *Aspergillus* and cystic fibrosis: old disease—new classifications. *Curr Opin Pulm Med* 2014; 20: 632-638.
42. Tang A, Sharma A, Jen R, et al. Inflammasome-mediated IL-1beta production in humans with cystic fibrosis. PLoS One 2012; 7: e37689.
43. Dubin P J, McAllister F, Kolls J K. Is cystic fibrosis a TH17 disease? Inflamm Res 2007; 56: 221-227.
44. Kreindler J L, Steele C, Nguyen N, et al. Vitamin D3 attenuates Th2 responses to *Aspergillus fumigatus* mounted by CD4+ T cells from cystic fibrosis patients with allergic bronchopulmonary aspergillosis. *J Clin Invest* 2010; 120: 3242-3254.

The invention claimed is:

1. A method of treating inflammation attributed to infection associated with cystic fibrosis in a patient, comprising administering to the patient in need thereof a pharmaceutical composition comprising Thymosin alpha 1.

2. The method of claim 1, further comprising administering to the patient at least one agent selected from the group consisting of antibiotic, antifungal, cystic fibrosis transmembrane conductance regulator (CFTR) corrector, CFTR potentiator, and anti-inflammatory agent.

3. The method of claim 2, wherein the antibiotic agent is selected from the group consisting of tobramycin, ciprofloxacin, and colistin.

4. The method of claim 2, wherein the antifungal agent is selected from the group consisting of itraconazole and amphotericin B.

5. The method of claim 2, wherein the CFTR corrector or potentiator agent is selected from the group consisting of ivacaftor and lumacaftor.

6. The method of claim 2, wherein the anti-inflammatory agent is ibuprofen.

7. The method of claim 2, wherein Thymosin alpha 1 and the at least one agent are administered to the patient together, separately, or sequentially.

8. The method of claim 1, wherein the pharmaceutical composition comprises one or more excipients and/or coadjuvants.

9. The method of claim 1, wherein the inflammation is chronic inflammation.

10. The method of claim 1, wherein the patient has a CFTR mutation ΔF508.

* * * * *

SEQUENCE LISTING

```
<160> NUMBER OF SEQ ID NOS: 2

<210> SEQ ID NO 1
<211> LENGTH: 28
<212> TYPE: PRT
<213> ORGANISM: Homo sapiens

<400> SEQUENCE: 1

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25

<210> SEQ ID NO 2
<211> LENGTH: 28
<212> TYPE: PRT
<213> ORGANISM: Artificial
<220> FEATURE:
<223> OTHER INFORMATION: scrambled peptide of SEQ ID NO:1

<400> SEQUENCE: 2

Ala Lys Ser Asp Val Lys Ala Glu Thr Ser Ser Glu Ile Asp Thr Thr
1               5                   10                  15

Glu Leu Asp Glu Lys Val Glu Val Lys Ala Asn Glu
            20                  25
```